United States Patent [19]

Schaefer

[11] Patent Number: 4,850,962

[45] Date of Patent: Jul. 25, 1989

[54] IMPLANTABLE HEARING AID AND METHOD OF IMPROVING HEARING

[75] Inventor: Donald W. Schaefer, Belleville, Wis.

[73] Assignee: Medical Devices Group, Inc., Madison, Wis.

[21] Appl. No.: 165,594

[22] Filed: Mar. 8, 1988

Related U.S. Application Data

[63] Continuation-in-part of Ser. No. 895,156, Aug. 11, 1986, Pat. No. 4,729,366, which is a continuation-in-part of Ser. No. 677,638, Dec. 4, 1984, abandoned.

[51] Int. Cl.$^4$ ............................................. H04R 25/00
[52] U.S. Cl. ................................... 600/25; 128/420.6
[58] Field of Search .................. 128/419 R, 421, 784, 128/789, 1 R, 420.5, 420.6; 381/68.3; 600/25

[56] References Cited

U.S. PATENT DOCUMENTS

| | | | |
|---|---|---|---|
| 3,170,046 | 2/1965 | Leale | 179/107 |
| 3,346,704 | 10/1967 | Mahoney | 179/107 |
| 3,557,775 | 1/1971 | Mahoney | 128/1 R |
| 3,712,962 | 1/1973 | Epley | 179/107 R |
| 3,764,748 | 10/1975 | Branch et al. | 179/107 E |
| 3,870,832 | 3/1975 | Frederickson | 179/107 E |
| 3,882,285 | 5/1975 | Nunley | 179/107 E |
| 4,150,262 | 4/1979 | Ono | 179/107 BC |
| 4,284,856 | 8/1981 | Hochmaier et al. | 179/107 E |
| 4,357,497 | 11/1982 | Hochmaier et al. | 179/107 E |

OTHER PUBLICATIONS

Jako, "Biomed Eng. in Ear Surgery", Otolaryngolic Clinics of N. America, vol. #5, Feb./72.
T. Ono—Implantable Hearing Aid (Pt 1), Audecibal, Fall '84.
Audiological Assessment of Vibratory Hearing, 17th Int. Congress of Audiology, Aug. '84, Santa Barbara, Calif.
Sako et al., "Conservative Tympanoplasty", Amer. Academy of Opthalmology & Otolarynology, Course 319, Oct. 1, 1966.
Article from The American Journal of Otology/vol. 5, No. 4, 4/84 entitled "Sound Pickup Utilizing an Implatable Piezoelectric Ceramic Bimorph Element—Application to the Cochlear Implant".
Article from "Hearing Instruments" vol. 32, No. 9, 1981/13 entitled "The Cochlear Implant: Performance of Deaf Patients"/Dr. House et al.
Copy of "Hearing Instruments" Jun. 1985 devoted to The Cochlear Implant—1985; Copies of all excerpts included.

*Primary Examiner*—Max Hindenburg
*Assistant Examiner*—J. P. Lacyk
*Attorney, Agent, or Firm*—Foley & Lardner

[57] ABSTRACT

A method and apparatus are disclosed for improving the hearing of a hearing-impaired subject who, if anatomically normal, possesses a tympanic membrane intended for generating mechanical tympanic vibrations in response to sound waves impinging thereon, an inner ear responsive to mechanical vibrations, and an ossicular chain intended to communicate mechanical vibrations from the tympanic membrane to the inner ear; wherein the ossicular chain is interrupted to preclude transmission of mechanical vibrations between the tympanic membrane and the inner ear of the subject and an implant is surgically interposed within the ossicular chain to form an independent link between the tympanic membrane and the inner ear, which implant is comprised of a transducer for converting mechanical signals generated at the tympanic membrane into electrical signals for direct electrical stimulation of the inner ear.

27 Claims, 5 Drawing Sheets

IMPLANTABLE HEARING AID AND METHOD OF IMPROVING HEARING

CROSS REFERENCE TO RELATED APPLICATION

This application is a continuation-in-part of application Ser. No. 895,156 filed Aug. 11, 1986, for which a U.S. Pat. No. of 4,729,366 and an issue date of Mar. 8, 1988 have been assigned, which is in turn a continuation-in-part of application Ser. No. 77,638 filed Dec. 4, 1984, now abandoned.

BACKGROUND OF THE INVENTION

The present invention relates to a device for improving the impaired hearing of a human subject, and more particularly, to an implantable hearing aid device.

In an anatomically normal human hearing apparatus, sound waves, which represent acoustical energy, are directed into an ear canal by the outer ear (pinna) and impinge upon a tympanic membrane (eardrum) interposed, at the terminus of the ear canal, between it and the middle ear space. The pressure of the sound waves effect tympanic vibrations in the eardrum, which then become manifested as mechanical energy. The mechanical energy in the form of tympanic vibrations is communicated to the inner ear by a sequence of articulating bones located in the middle ear space, which are generally referred to as the ossicular chain. The ossicular chain must be intact if acoustical energy existing at the eardrum is to be conducted as mechanical energy to the inner ear.

The ossicular chain includes three primary components, the malleus, the incus and the stapes. The malleus includes respective manubrium, neck and head portions. The manubrium of the malleus attaches to the tympanic membrane at a point known as the umbo. The head of the melleus, connected to the manubrium by the neck portion, articulates with one end of the incus, which provides a transmission path for the mechanical energy of induced vibrations from the malleus to the stapes. The stapes includes a capitulum portion connected to a footplate portion by means of a support crus and is disposed in and against a membrane-covered opening to the inner ear referred to as the oval window. The incus articulates the capitulum of the stapes to complete the mechanical transmission path.

Normally, tympanic vibrations are mechanically conducted through the malleus, incus and stapes, to the oval window and therethrough to the inner ear (cochlea). These mechanical vibrations generate fluidic motion (transmitted as hydraulic energy) within the cochlea. Pressures generated in the cochlea by fluidic motion are accommodated by a second membrane-covered opening between the inner and middle ear, referred to as the round window. The cochlea translates the fluidic motion into neural impulses corresponding to sound perception as interpreted by the brain. However, various disorders of the tympanic membrane, ossicular chain and/or inner ear can occur to disrupt or impair normal hearing.

Various passive mechanical ossicular prosthesis and implantation techniques have been developed in connection with reconstructive surgery of the middle ear. See G. J. Jako, "Biomedical Engineering in Ear Surgery", *Otolaryngoloqic Clinics of North America*, Vol. 5, No. 1, Feb. 1972, and G. J. Jako, et al., "Conservative Tympanoplasty", American Academy of Opthalmology and Otolaryonology, Course 319, presented Oct. 1, 1966.

Miniaturized electronic hearing aid devices which compensate for hearing disorders are also, in general, well known. Various of such devices are adapted to be entirely received within the ear canal or partly or completely implanted within the skull of a subject. Examples of such devices are those disclosed in U.S. Pat. Nos. 3,170,046, issued to L. P. Leale on Feb. 16, 1965; 3,712,962 issued to J. M. Epley on Jan. 23, 1973; 3,764,748 issued to J. P. Branch et al. on Oct. 9, 1973; 3,346,704 and 3,557,775 issued on Oct. 10, 1967 and Jan. 26, 1971, respectively to J. L. Mahoney; 3,870,832 issued to J. M. Fredrickson on Mar. 11, 1975; 4,150,262 issued to H. Ono on Apr. 17, 1979; 4,284,856 and 4,357,497 both issued to I. J. Hochmaier et al. on Aug. 18, 1981 and Nov. 2, 1982, respectively. Further description of such devices is found in T. Ohno, "The Implantable Hearing Aid" (Part I) Audecibel, Fall 1984 and Aritomo et al., "Audiological Assessment of Vibratory Hearing" presented at 17th International Congress of Audiology meeting, Santa Barbara, Calif., Aug. 1984. See also, K. Gyo, N. Yanagihara, and H. Araki, "Sound Pickup Utilizing an Implantable Piezoelectric Ceramic Bimorph Element: Application to the Cochlear Implant", American Journal of Ontology, Vol. 5, No. 4, April 1984.

Perhaps the most interesting of the aforementioned United States patents is the '748 patent which concerns implantable hearing aids including those which are configured for disposition principally within the middle ear space. The approach suggested there provides a transducer, which may be a piezoelectric crystal transducer, capable of converting mechanical vibration within the ossicular chain into an output voltage. That output voltage may be applied to the area of the oval window to electrically stimulate it and may include a diode to rectify the variable voltage output of the transducer into a pulsating DC voltage to stimulate the auditory nerve. In another variant, the patentees suggest the incorporation of a piezoelectric crystal in the area of the oval window which receives the variable voltage signals from the transducer and vibrates to stimulate the auditory nerve. In any of these approaches, however, the proposed system also utilizes what the patentees regard as the natural distortion-free transmission of sound through the ossicular chain wherever possible. They say that, by virtue of leaving the ossicular chain intact, the acoustic energy impinging upon the eardrum passes through the ossicular chain in a distortion-free manner whereby the sound powered hearing aid they describe needs only supply minimal assistance to the hearing process. The description continues in the '748 patent to note that, as an alternative, the stapes may be removed and the hearing aid physically located in its stead where conditions permit. Under those circumstances, where the stapes is removed, the end of the incus is free-standing and the hearing aid is physically associated with it, such as by means of claimable rings or the like. Thus the hearing aid serves as an integral part of the mechanical linkage in the transmission of forces from the eardrum to the oval window in all events, whether or not the integrity or continuity of the ossicular chain remains unimpaired. That being the case, mechanical feedback through the ossicular chain is a likely consequence, diminishing the overall efficacy of the approach suggested there.

Another example of an implantable hearing aid is described in U.S. Pat. No. 3,882,285 issued to J. A. Nunley et al. on May 6, 1975 and commonly assigned with the present invention. In accordance with the Nunley et al. invention, a self-contained miniature hearing device is implanted in the skull just behind the ear (pinna). The device includes a transducer, such as a microphone, a microphone port, an amplifier and a transmitter for providing a mechanical response to the sound received by the microphone. The microphone port is positioned in the ear canal. The transmitter of the preferred exemplary embodiment of Nunley et al. utilizes a piezoelectric crystal connected to the ossicular chain, preferably to the stapes.

An alternative hearing aid design, the cochlear implant, has received a modest amount of attention in the prior art. The cochlear implant is an electronic device that allows profoundly deaf people to "hear" by electrical stimulation of the auditory nerve fibers within the inner ear. A typical system includes an external microphone, signal processor and transmitter, and an implanted receiver and electrode. The microphone transponds normal sound waves, converting this mechanical sound energy into electrical energy representative thereof. The processor amplifies the electrical energy, filters it and sends it to the transmitter, which changes the electrical signals into magnetic signals. Transcutaneous magnetic currents cross the skin and are received by the implanted receiver, a coil for example, and the signal travels to the cochlea via a wire electrode. Current flows between this active electrode and a nearby ground electrode, preferably disposed in the eustacian tube, to stimulate nerve fibers present in the cochlea. The brain interprets this stimulation as sound. See T. Kriewall, "Why Combine Multichannel Processing With A Single Electrode", Hearing Instruments, June 1985; W. House, D. Bode, and K. Berliner, "The Cochlear Implant: Performance of Deaf Patients", Hearing Instruments, September 1981 (both issues of the above cited publications focus entirely on cochlear implants and are incorporated herein and relied upon). See also U.S. Pat. No. 3,764,748, discussed above, for a variation on this theme.

The prior art systems, however, admit of room for improvement in that these known devices tend to be susceptible to interference by extraneous sounds and/or distortion of the sound ultimately perceived by the subject. Other prior art systems utilize air-induced microphones disposed to be responsive to soundwaves for generating an electrical signal from which the stimulus to the inner ear is ultimately derived. Air-induced microphones are disadvantageous in that the microphone is typically either disposed external to the skull or requires a percutaneous element such as a microphone port or connecting wire. Moreover, the frequency response of air-induced microphones tends not to provide sufficient frequency range for realistic fidelity, and such microphones typically do not provide constant frequency sensitivity across their frequency band.

In the aforementioned presentation, "Conservative Tympanoplasty" by Jako et al., it was proposed that a relatively large piezoelectric crystal pickup transducer be built into the place of the tympanic membrane and directly drive a smaller piezoelectric crystal output transducer placed in the oval window. See Jako et al., supra, at pages 53–54. However, the Jako et al. system has reportedly never been reduced to practice, and the practicability of the system was noted as questionable by the authors themselves (See p. 53).

SUMMARY OF THE INVENTION

The present invention provides a method and apparatus for improving the impaired hearing of a subject utilizing a device manifesting a frequency response commensurate with that provided by normal hearing. In accordance with one aspect of the present invention, the mechanical vibrations effected by the tympanic membrane (eardrum) are converted into electrical signals which are thereafter amplified and converted into mechanical vibrations and communicated to the inner ear. Conversion of mechanical energy to electrical energy is achieved by means of an input transducer which is surgically implanted within the ossicular chain, followed by suitable amplification of those electrical signals to account for both the level of hearing impairment suffered by the subject and the electromechanical response of the implanted device. In one implementation of the present invention, the signals are converted to mechanical energy (vibrations) once again by an output transducer, all to achieve the desired level of aural enhancement for the wearer. These transducers and the associated circuitry thus comprise means for mediating mechanical/electrical energy within the middle ear space. In another preferred implementation, the electrical output of the transducer is suitably conditioned and applied as a direct electrical stimulus to or proximate the cochlea. In all instances the ossicular chain of the subject is interrupted to preclude transmission of mechanical vibrations between the tympanic membrane and the inner ear, with the implanted device interposed within the chain to bridge the interruption therein and form an electromechanically independent link, free from feedback, between the membrane and the inner ear.

In a particularly preferred variant of the present invention, the implanted device includes an input transducer means operatively associated with or proximate the eardrum for receiving mechanical tympanic vibrations therefrom and converting them into electrical signals characteristic of the acoustic energy creating those vibrations. Those signals are applied to appropriate electronic circuitry to amplify and perhaps otherwise control or condition them as may be required or found desirable. Those signals are then communicated to the inner ear, for example by electrode penetration of the oval window or round window, or by direct electrical stimulation of the promontory, a bony bulge in the wall of the tympanic cavity (middle ear space) defined by the region in which the cochlea protrudes into the cavity. The transducers may be of any convenient and efficient design, including piezoelectric film transducers, piezoelectric crystal force transducers, piezoelectric accelerometers, or electromagnetic transducers. Preferred are the piezoelectric transducers, and most preferred is a piezoelectric transducer in an accelerometer configuration.

BRIEF DESCRIPTION OF THE DRAWING

Preferred exemplary embodiments of the present invention will hereinafter be described in conjunction with the appended drawing wherein like designations denote like elements and.

DETAILED DESCRIPTION OF A PREFERRED EXEMPLARY EMBODIMENT

Figure 1:
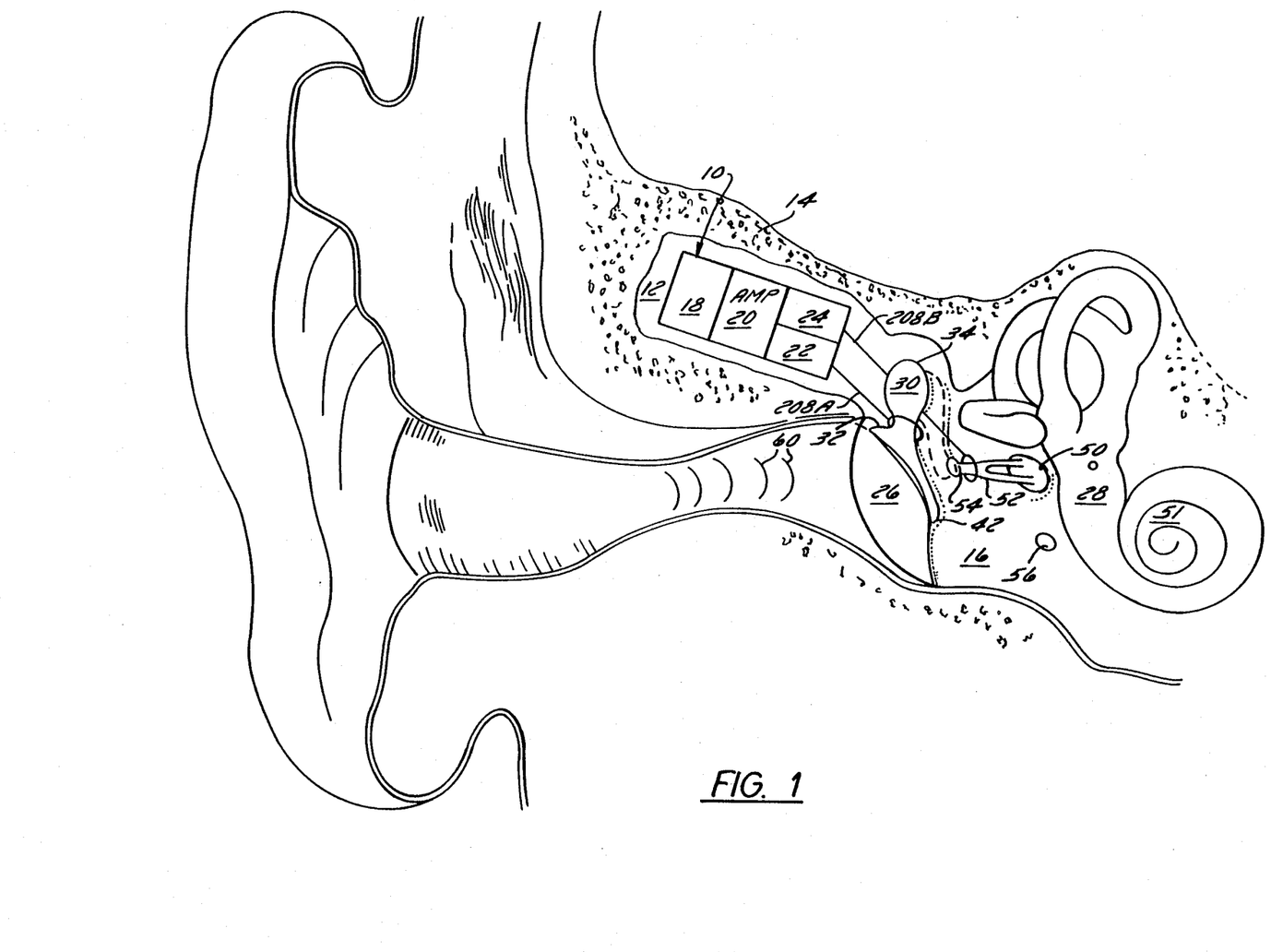
FIG. 1 is a schematic section through a portion of the skull of a human subject adjacent to the ear showing the disposition of one embodiment of an implantable hearing aid in accordance with the present invention.

Referring to FIG. 1, a first embodiment 10 of an implantable hearing device in accordance with the present invention is shown disposed in a surgically developed antrum 12 in the mastoid bone of the subject's skull 14, communicating with the subject's middle ear space 16. Device 10 in this embodiment is comprised of a power source 18, an amplifier 20, a mechanical to electrical input transducer 22 and an electrical to mechanical output transducer 24.

Figure 2:
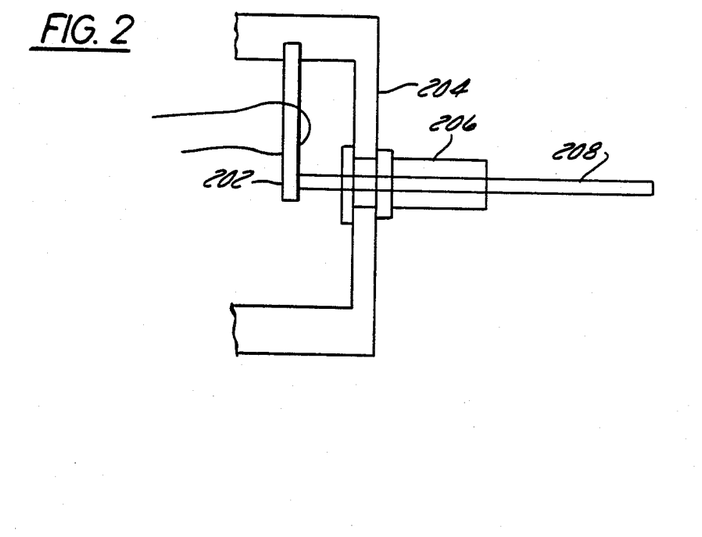
FIGS. 2-5 are schematic illustrations of respective alternative mechanical connections between the transducers and the hearing apparatus of the subject.

Referring briefly to FIG. 2, input transducer 22 and output transducer 24 suitably each comprise a piezoelectric element 202 cooperating with a resilient diaphragm 204. A connecting member 208, mounted on and maintained by diaphragm 204, is operatively coupled to piezoelectric element 202. Connecting member 208 advantageously is a 0.005 inch diameter stainless steel wire. (The respective wires 208 associated with input transducer 22 and output transducer 24 will be referenced as 208A and 208B, respectively.) A sleeve 206, mounted to housing 204, and slideable retaining wire 208 may be employed to prevent lateral movement and dampen any spurious vibrations.

Input transducer 22 cooperates with tympanic membrane 26 and converts tympanic vibrations corresponding to sound into electrical signals. Input transducer 22, in effect, utilizes tympanic membrane 26 in a manner similar to the diaphragm of a microphone. With reference now to FIGS. 1 and 2, the input transducer 22 is mechanically coupled to tympanic membrane 26, suitably by connecting stiff wire 208A to the subject's malleus 30. Connecting wire 208A may be affixed to malleus 30 utilizing surgical techniques similar to those used in ossicular reconstructive surgery, or by other desirable techniques or mechanisms. Examples of connection mechanisms will be described in conjunction with FIGS. 3-5. When sound waves, generally indicated as 60, impinge upon tympanic membrane 26, corresponding tympanic vibrations are initiated. The vibrations are transmitted to malleus 30, and therefrom, through wire 208A to input transducer 22. The mechanical vibrations are converted by piezoelectric element 202 (FIG. 2) to electrical signals. The electrical signals are then applied as input signals to amplifier 20.

The use of the tympanic membrane as an operative portion of the input transducer is particularly advantageous. On the one hand, permanently percutaneous elements, e.g. wires, ports to the ear canal, etc., typically associated with other input mechanisms such as air-induced microphones, are avoided, and this can be important in many situations. In any event, without regard to the avoidance of percutaneous elements, a principal operational advantage is realized because the frequency response of the input transducer is in main part determined by the tympanic membrane and other characteristics of the individual subject's hearing mechanism and thus tends to more nearly approximate the frequency response of the subject's normal aural apparatus.

Amplifier 20 operates on the input transducer electrical output signals to generate corresponding amplified input signals to output transducers which are of sufficient magnitude to drive the output transducer element 202, and which compensate for deficiencies in the frequency sensitivity of the subject. Amplifier 20 is typically of the thin film type and suitably comprises any conventional amplifier circuit having input and output electrical impedances in accordance with the electrical impedances of transducers. The frequency response of the amplifier circuit is shaped, as is well known in the art, to compensate for frequency sensitivity deficiencies of the subject. The magnitude of the output signals from amplifier 20 is also limited to a predetermined maximum value to prevent possible injury (acoustic trauma) to the inner ear. The power source 18 for amplifier 20 is preferably a long life lithium type battery.

Output transducer 24 is utilized to convert the amplified electrical signals representing the tympanic vibrations into mechanical vibrations for application to the inner ear 28 of the subject. The amplified electrical signals are applied as input signals to the piezoelectric element 202 of output transducer 24 and are converted into corresponding mechanical vibrations. The vibrations are communicated to the inner ear by a mechanical connection between wire 208B and the oval window 50 or round window 56, and therethrough to the cochlea 51. The connection between wire 208B and the inner ear can be made in a manner similar to techniques employed in reconstructive surgery using passive mechanical prosthesis deices or by any other suitable mechanism. Exemplary connections will be described in connection with FIGS. 3-5.

As noted above, the mechanical connections between input transducer 22 and tympanic membrane 26 and between output transducer 24 and inner ear 28 are effected utilizing surgical techniques similar to those used in ossicular reconstructive surgery, or by other desired methods. The connections are suitably made by affixing the distal end of stiff wire 208 to an appropriate portion of the ossicular chain, and a portion of the ossicular chain is then utilized as an integral part of the mechanical connection.

Figure 3:
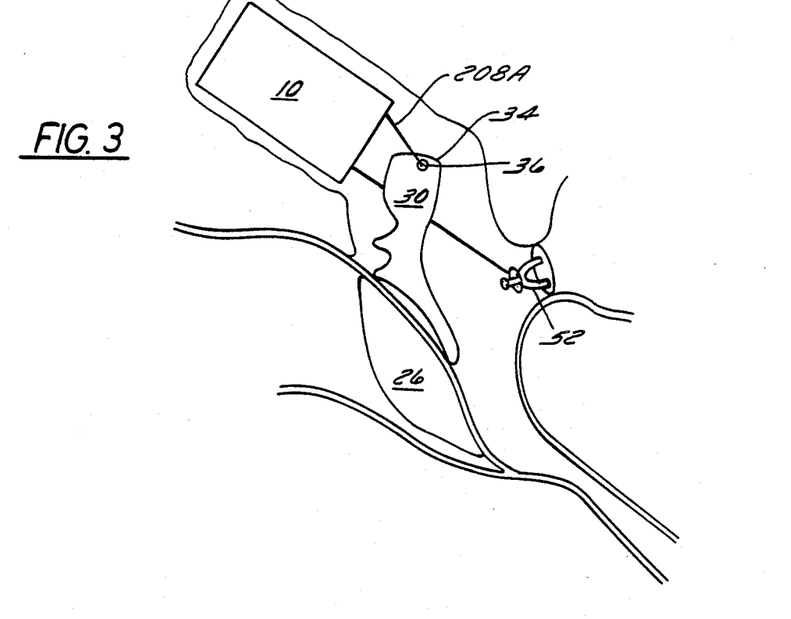
Figure 4:
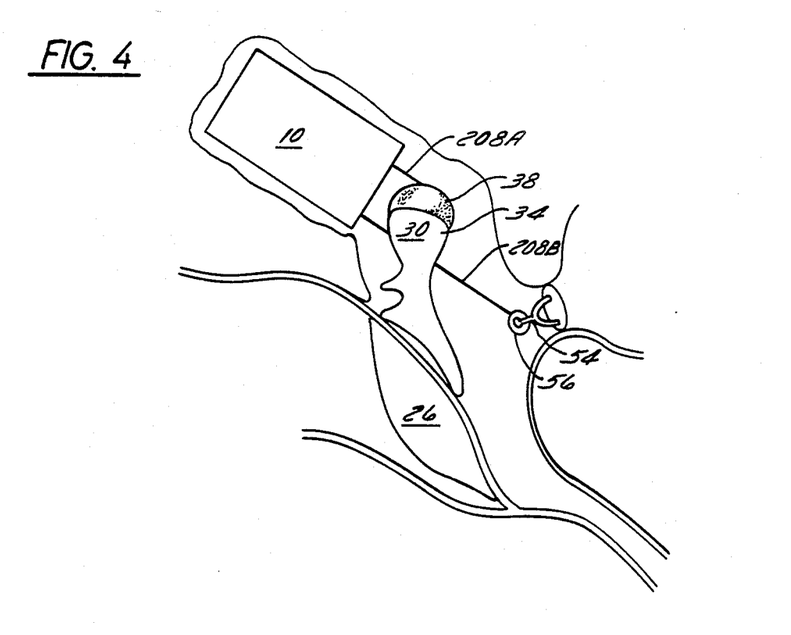
Figure 5:
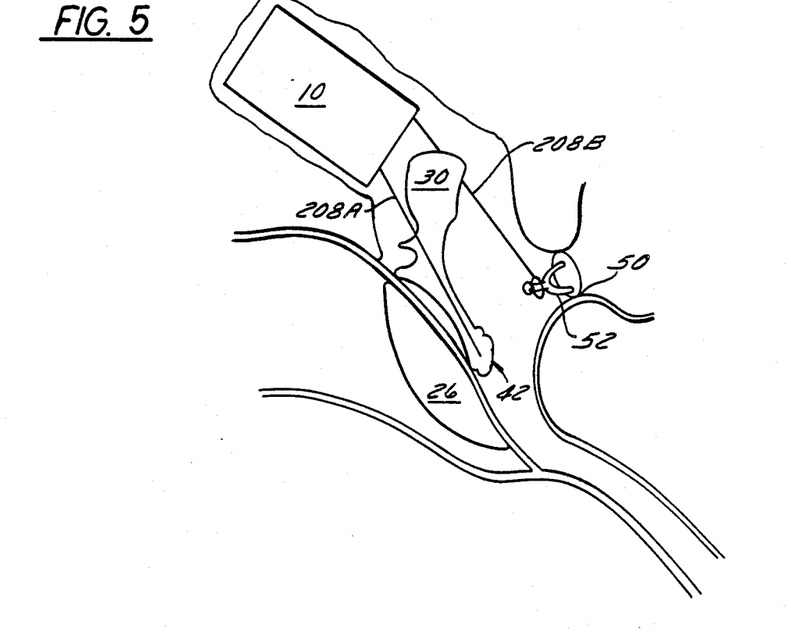

With respect to input transducer 22, the distal end of wire 208A is shown to be affixed to the subject's malleus 30, preferably to the head 34 of malleus 30. For example, as shown in FIG. 3, a small hole 36 may be drilled in the malleus head 34 and the distal end of wire 208A received and secured in hole 36. Wire 208A may be secured by suitable biocompatible cement such as an acrylate ester or fibrin cement. In some instances, wire 208A may be fixed to malleus head 34 solely through use of a biocompatible cement without the necessity of hole 36. Alternatively, as schematically shown in FIG. 4, the coupling to malleus 30 can be effected through use of an intermediary fitting (cap) 38, articulating with malleus head 34. It may, however, be desirable in some circumstance to affix wire 208A to portions of the malleus 30 other than head 34. For example, as shown in the embodiment of FIG. 1, the distal end of wire 208A may be looped about the neck 32 of malleus 30. Alternatively, wire 208A may be coupled to the tip of the manubrium 42 of malleus 30. Such a connection is schematically shown in FIG. 5. The attachment is preferably effected utilizing biocompatible cement as noted above, or by drilling a hole in manubrium 42 for receiving the distal end of wire 208A.

With respect to output transducer 24, the distal end of wire 208B is suitably affixed to the subject's stapes 52. As schematically shown in FIG. 1, the distal end of wire 208B may be looped about the capitulum 54 of stapes 52, or, as schematically shown in FIG. 4, an intermediate fitting 56 articulating with capitulum 54 may be employed. Likewise, the connection can be effected utilizing biocompatible cement. In some instances, it may be desirable to effect a connection between 208B and the crus or footplate portions of the stapes or directly to the oval window in accordance with well known reconstructive surgical techniques.

It may, however, be desirable in some circumstances, to effect a connection between wire 208B and the round window 56 rather than to the oval window. A direct connection to the round window input to the cochlea may be effected utilizing a device fashioned from biocompatible materials simulating a footplate disposed over the round window membrane, to which wire 208B is attached.

Figure 6:
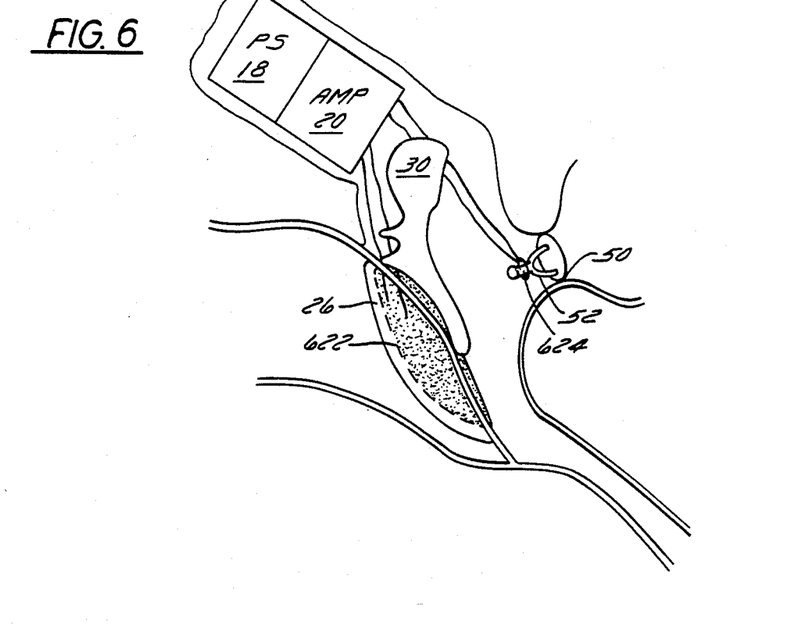
FIG. 6 is a schematic illustration of a further embodiment of the present invention utilizing polymeric piezoelectric film transducers.

In accordance with another embodiment of the present invention, one or both of input transducer 22 and output transducer 24 can be formed from a polymeric piezoelectric film such as polyvinylidene fluoride (PVDF) disposed directly on an appropriate element of the subject's physical hearing apparatus and electrically connected to amplifier 20. One such embodiment of the present invention is illustrated in FIG. 6, wherein respective PVDF film 622 and 624 are utilized as the input and output transducers, respectively. Input transducer PVDF film 622 is disposed on the inner surface of tympanic membrane 26, underlying the manubrium 42 of malleus 30. Alternatively, PVDF film 622 could be disposed on malleus 30, preferably on the underside of the manubrium or otherwise interposed between the tympanic membrane 26 and the underside of the manubrium of malleus 30. Film 622 is electrically connected to the input terminals of amplifier 20.

Input transducer PVDF film 624 is disposed on stapes 52, or directly on oval window 50 or round window 56, and is electrically connected to the output terminals of amplifier 20. When soundwaves impinge on tympanic membrane 26 and generate tympanic vibrations, such vibrations are sensed by film 622 and converted into electrical signals for application to amplifier 20. The amplified electrical signals are then applied to output transducer film 624 which converts the amplified signals into mechanical vibrations for transmission to the inner ear.

The ossicular chain is broken in implementing the present invention to prevent positive feedback of the amplified vibrations to the input transducers from occurring. The break would typically be effected by removing at least one of the component parts of the ossicular chain, typically the incus. It is desirable to maintain the malleus and stapes in normal anatonomical position with muscle and tendon intact to maintain the subject's natural defense mechanism against acoustic trauma.

Figure 7:
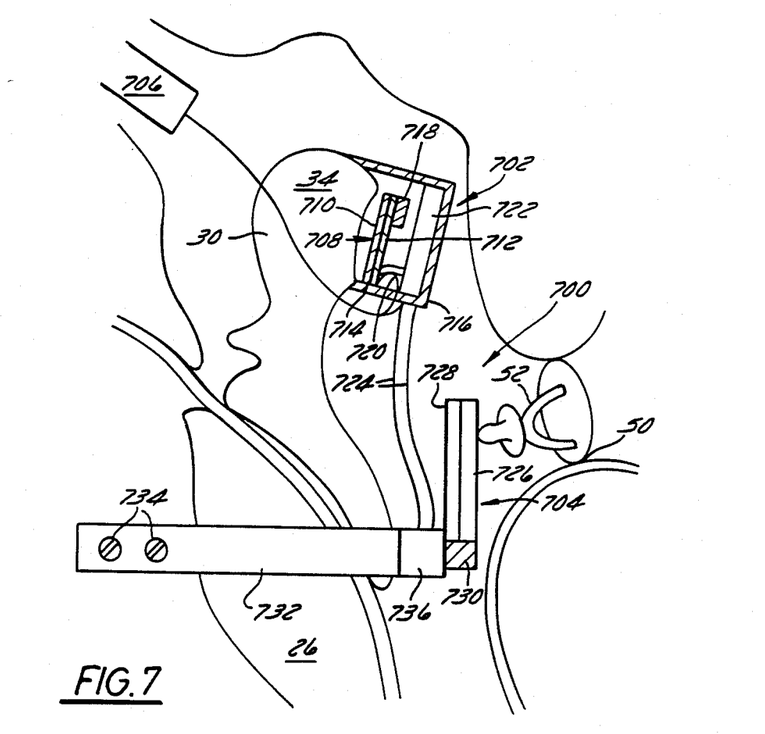
FIG. 7 is a schematic illustration, partly in section, of a preferred alternate embodiment, showing a transducer in an accelerometer configuration.

FIG. 7 illustrates an alternate embodiment of an implantable hearing aid 700 in accordance with the present invention. The hearing aid 700 is comprised of paired transducer means for mediating electrical/mechanical signals, in this instance a first or input transducer means designated generally as 702 and a second or output transducer means designated generally as 704. The transducers are powered by a power supply 706 disposed within an antrum formed in the bony structure proximate the ear of the subject receiving the implant. The input transducer 702 is operatively associated with the head 34 of the malleus 30 which vibrates in response to movement of the eardrum as acoustical energy impinges upon it. The transducer 702 in this embodiment is shown to be in the configuration of a piezoelectric accelerometer, comprised of a piezoelectric bimorph 708 having a first piezoelectric crystal element 710 lying in generally face-to-face relationship with an opposed crystal 712. The bimorph 708 is cantilevered at its first end 714 from an enveloping structure or implanting shield 716, the terminal edges of which are secured to the head 34 of malleus 30 by means of a suitable biocompatible adhesive or other surgically acceptable means. The accelerometer configuration is achieved in this embodiment by a structural weight 718 secured to one of the crystals such as crystal 712 at the end opposite that cantilevered from the implanting shield 716. In this configuration, when the malleus vibrates coincident with tympanic vibrations the weight 718 imparts an inertial response to the bimorph 708 which will itself then vibrate in a mechanical pattern replicating the vibration of the malleus. Recognizing that the forces extant the tympanic membrane have been determined to be extraordinarily intense, beyond that previously appreciated, the accelerometer configuration offers enhanced efficiency. Then too, since the bimorph 708 is cantilevered or otherwise anchored directly from the mounting structure, the problems inherent in the placement of these types of elements within a mucuous membrane environment are greatly alleviated.

Vibrations in the accelerometer are converted to electrical signals as a consequence of the inherent characteristics of piezoelectric crystals. These electric signals are applied via signal leads 720 to an amplifier 722. Depending upon the characteristics of the amplifier 722, a suitable or sufficient gain may be realized allowing those electric signals to be applied directly to the output or second transducer 704; otherwise the amplifier 722 may be used as a preamp and a separate amplifier associated with the transducer 704 will be provided. Regardless, the signals from amplifier 722 are routed through the middle ear space via signal lines 724 for ultimate application to the output transducer. In this context, the signal leads along with the associated amplifier circuitry thus constitute transmission means for communicating between the input and output transducers in lieu of communication through the ossicular chain.

The output transducer of this embodiment is a bimorph piezoelectric crystal structure comprised of a pair of piezoelectric crystals 726 and 728 cantilevered at a first end from a support element 730. The support element 730 is mounted on an arm 732 secured to a bony region of the subject by means of fixture elements 734, such as surgical screws. This fixturing approach is conceived to be most reliable physically and functionally due to the difficulty of implanting devices in the mucous membrane environment of the middle ear. The mounting member 732 thus places the output transducer 704 in proximate contact with the stapes 52 whereby vibrations in the output transducer 704 are communicatively coupled thereto. Depending upon the electrical characteristics of the amplifier 722 as noted above, an optional amplifier 736 may be provided for driving the output transducer 704. These matters, however, which can be tailored at the time the device and its associated circuitry are designed.

As is evident from the description of the structure in FIG. 7, it can be seen that the transducers 702 and 704 are surgically interposed within the ossicular chain in replacement, in this instance, of the incus. The transducers and associated circuitry bridge the interruption in the ossicular chain resultant from removal of the incus to form an independent link between the tympanic membrane and the inner ear. In this fashion the potential for mechanical feedback is entirely eliminated, resulting in both improved efficiencies and comfort to the subject. And, when it is the incus which is removed in order to interrupt the ossicular chain and prevent transmission of mechanical vibrations, the skeletomuscular network of the subject maintains the natural defense mechanism against acoustic trauma should excessively loud noises be encountered.

Figure 8:
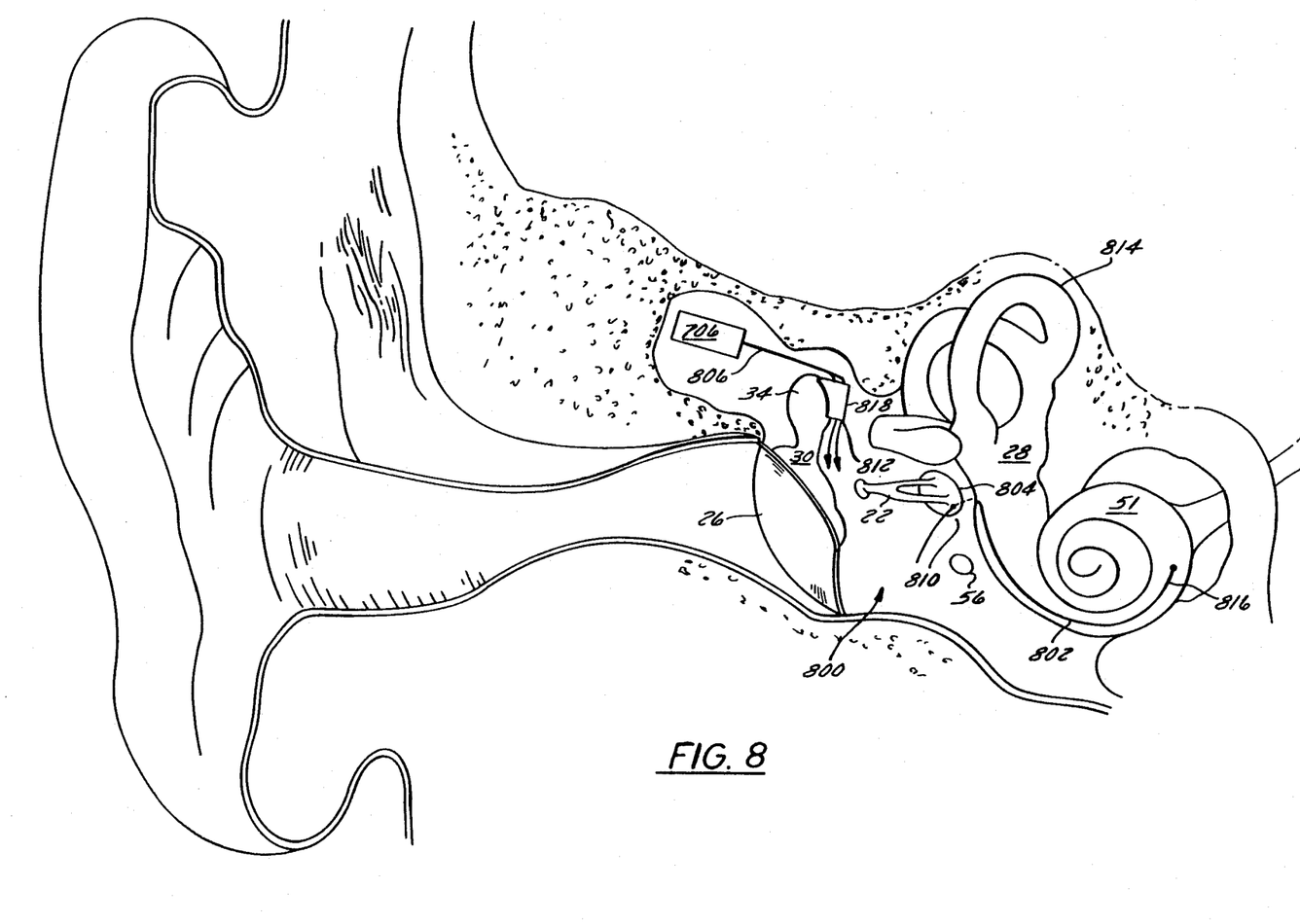
FIG. 8 is a schematic illustration of a further preferred embodiment of the present invention utilizing an accelerometer, having wires leading to a power supply, and an electrode, shown penetrating the cochlea through the footplate of the stapes and the oval window.

FIG. 8 illustrates an alternate and highly preferred embodiment of an implantable hearing aid 800 in accordance with the present invention in which a modified hearing response is effected by direct electrical stimulation of the inner ear. Hearing aid 800 is comprised of a single transducer means 818 secured to malleus 30 by conventional surgical procedures. Transducer 818 is powered by a power supply 706, preferably disposed within an antrum formed in the bony structure proximate the subject's ear. Power supply 706 is shown connected to transducer 818 by electrical connection 806. If power supply 706 cannot the conveniently disposed intracranially, percutaneous electromagnetic transmission of the electrical signal to an external power source may be employed.

Transducer 818 is operatively associated with the head 34 of malleus 30 which vibrates in response to movement of the eardrum as sound waves impinge thereon. Transducer 818 is preferably comprised of a piezoelectric accelerometer in accordance with the above-described bimorph configuration (see description of the embodiment of FIG. 7). In contrast to the above-described embodiments, however, the electrical signals produced by transducer 818 are not converted back into mechanical signals; rather, the electrical signals themselves stimulate cochlea 51 directly to effect a modified hearing response. Notwithstanding the fact that the coupled transducer configuration disclosed above is truncated in this embodiment, for direct electrical stimulus of the auditory nerve, the hiatus created in the ossicular chain once again precludes feedback or competing paths between the tympanic membrane and the cochlea.

Hearing aid 800 further comprises transmission means 802, which may be a wire electrode, having a proximal end 812 disposed in operative communication with transducer 818, and a distal end 816 disposed in electrical communication with inner ear 28. Inner ear 28, or the labyrinth, is comprised of an upper portion 814 (the vestibule), which controls equilibrium and balance, and a lower portion 51 (the cochlea), which is the auditory portion related to hearing. Auditory nerve fibers are located along the inner walls of cochlea 51, and are collectively referred to as the organ of Corti. Electrical stimulation of the auditory nerve fibers is achieved via invasion of cochlea 51 by transmission means 802.

In one preferred method, stapes 22 is removed and distal end 816 of transmission means 802 is disposed in cochlea 51 by penetrating the oval window membrane located on promontory 810 beneath foot plate 804 of stapes 22. Alternatively, stapes 22 remains in place and a hole is drilled in foot plate 804 of stapes 22, using conventional surgical techniques. Distal end 816 of transmission means 802 is then guided through the hole, through oval window membrane, and into cochlea 51, as shown in FIG. 8. In yet another alternate embodiment, stapes 22 is left intact, and distal end 816 of transmission means 802 invades cochlea 51 through round window 56.

If penetration of the cochlea is undesirable, electrical stimulation of cochlea 51 may nonetheless be effected; distal end 816 of transmission means 802 may be secured to the middle ear cavity membrane along promontory 810 by conventional surgical techniques.

It will be understood that the above description is of preferred exemplary embodiments of the present invention and that the invention is not limited to the specific forms shown. For example, it is not necessary that each of the components in the embodiment of FIG. 1 be disposed in a unitary housing. Rather, the various components can be physically separated. Further, the respective components may in some instances be disposed in the natural middle ear space of the subject, rather than in a surgically developed antrum. These and other modifications may be made in the design and arrangement of the components without departing from the spirit of the invention as expressed in the appended claims.

What is claimed:

1. A method for improving the hearing of a hearing-impaired subject, said subject, if anatomically normal, having a tympanic membrane for generating mechanical tympanic vibration in response to sound waves impinging thereon, an inner ear capable of phonoreception, and an ossicular chain comprising an incus, a malleus, and a stapes, intended for communicating mechanical vibrations from said tympanic membrane to said inner ear, said method comprising the steps of:

interrupting said ossicular chain to preclude transmission of said mechanical vibrations between said tympanic membrane and said inner ear of said subject; and, surgically interposing an implant within said ossicular chain, between said tympanic membrane and said inner ear to facilitate electrical stimulation of the auditory nerve, said implant comprising:

transducer means for converting said mechanical vibrations to electrical signals, having controlled amplification characteristics; and transmission means for communicating said electrical signals from said transducer means to said inner ear;

wherein said transducer means includes means operatively associated with said tympanic membrane for receiving mechanical tympanic vibrations therefrom and converting the same into electrical signals characteristic thereof.

2. The method of claim 1, wherein said interrupting step comprises removing at least one of the component parts from said ossicular chain.

3. The method of claim 2, wherein said interrupting step comprises removing the incus from the ossicular chain.

4. The method of claim 1, wherein said step of surgically interposing said implant comprises disposing a mechanical to electrical transducer, for generating electrical signals characteristic of said mechanical vibrations of said tympanic membrane, within the middle ear space of said subject; and     effecting a mechanical connection between an element of the ossicular chain and said transducer.

5. The method of claim 4, wherein said step of effecting a mechanical connection comprises mounting said transducer on the malleus.

6. The method of claim 4, wherein said step of effecting a mechanical connection comprises mounting said transducer on the head of said malleus.

7. The method of claim 4, wherein said transducer comprises a piezoelectric accelerometer.

8. The method of claim 1, wherein said implant further comprises a power source.

9. The method of claim 1, further comprising the step of disposing a power source, for supplying power to said implant, external to said subject.

10. The method of claim 1, wherein said transmission means comprises a proximal end in operative electrical communication with said transducer means and a distal end in electrical communication with said inner ear for transmitting electric signals from said transducer to said inner ear.

11. The method of claim 10, wherein said step of surgically interposing said implant comprises disposing said distal end of said transmission means within the cochlea of said subject proximate the auditory nerve fibers thereof for electrical stimulation of said nerve fibers to represent sound energy impinging on said tympanic membrane.

12. The method of claim 11, wherein said step of disposing said distal end of said transmission means in said cochlea comprises the steps of removing the stapes and penetrating the oval window to facilitate invasion of the interior of said inner ear by said transmission means.

13. The method of claim 11, wherein said step of disposing said distal end of said transmission means comprises the steps of:

drilling a hole in the footplate of said stapes;
    guiding said distal end of said transmission means through said hole; and
    penetrating the oval window to effect invasion of the interior of said inner ear by said transmission means.

14. The method of claim 11, wherein the step of disposing said distal end of said transmission means comprises penetrating the round window to effect invasion of the interior of said inner ear by said transmission means.

15. The method of claim 10, wherein said step of disposing said transmission means in said cochlea comprises the step of securing said distal end of said transmission means to the promontory to establish electrical communication between said transducer means and said inner ear.

16. An implantable apparatus for improving the hearing of a hearing-impaired subject, said subject, if anatomically normal, having a tympanic membrane for generating mechanical tympanic vibrations in response to sound waves impinging thereon, and an ossicular chain comprising an incus, a malleus, and a stapes for communicating said tympanic vibrations to the inner ear of said subject, said apparatus comprising:

transducer means for converting said tympanic vibrations to electrical signals, having controlled amplification characteristics, configured for bridging disposition in an interrupted ossicular chain of said subject as an independent electromechanical link between said tympanic membrane and said inner ear of said subject, said transducer means disposed in operative association with said tympanic membrane for receiving mechanical tympanic vibrations therefrom and converting the same into electrical signals characteristic thereof; and     transmission means for communicating said electrical signals from said transducer means to said inner ear for effecting electrical stimulation thereof.

17. The apparatus of claim 16, further comprising a power supply electromagnetically associated therewith.

18. The apparatus of claim 17, wherein said power supply is disposed externally of said subject.

19. The apparatus of claim 16, wherein said transmission means comprises:

an electrical conduit having a proximal end in operative electrical communication with said transducer means and a distal end in operative electrical communication with said inner ear.

20. The apparatus of claim 16, wherein said transducer means is disposed proximate said malleus for operative association therewith.

21. The apparatus of claim 20, wherein said transducer means is mounted on the head of said malleus.

22. The apparatus of claim 20, wherein said transducer means is a piezoelectric accelerometer.

23. The apparatus of claim 19, wherein said transmission means is an electrically conductive wire.

24. The apparatus of claim 19, wherein said distal end of said transmission means is configured for electrical contact with the promontory.

25. The apparatus of claim 19, wherein said distal end of said transmission means is disposed interiorly of said inner ear.

26. The apparatus of claim 25, wherein said distal end of said transmission means extends through the stapes, through the oval window, and into said inner ear.

27. The apparatus of claim 25, wherein said distal end of said transmission means extends through the round window and into said inner ear.

* * * * *